United States Patent [19]

Laüterjüng

[11] Patent Number: 4,522,623
[45] Date of Patent: Jun. 11, 1985

[54] SUCTION BOTTLE FOR MEDICINAL PURPOSES

[76] Inventor: Friedrich G. Laüterjüng, Schallstr. 6, 5000 Köln 41, Fed. Rep. of Germany

[21] Appl. No.: 447,558

[22] Filed: Dec. 7, 1982

[30] Foreign Application Priority Data

Dec. 21, 1981 [DE] Fed. Rep. of Germany ....... 3150500

[51] Int. Cl.³ ............................................. A61M 1/00
[52] U.S. Cl. .................................. 604/319; 128/760; 137/205
[58] Field of Search ...................... 128/760; 141/8, 59, 141/51, 67, 95; 220/319; 604/317–324, 326; 433/97; 137/205

[56] References Cited

U.S. PATENT DOCUMENTS

| | | | |
|---|---|---|---|
| 2,194,004 | 3/1940 | Bukolt | 220/319 |
| 2,815,621 | 12/1957 | Carter | 141/51 |
| 3,646,935 | 3/1972 | Holbrook et al. | 604/319 |
| 4,058,123 | 11/1977 | May | 60/30 |
| 4,289,158 | 3/1981 | Nehring | 137/205 |
| 4,346,711 | 8/1982 | Agdanowski et al. | 604/319 |
| 4,430,084 | 2/1984 | Denton | 604/317 |

FOREIGN PATENT DOCUMENTS 1810801  6/1970  Fed. Rep. of Germany .
2840865  3/1980  Fed. Rep. of Germany .

OTHER PUBLICATIONS

Catalog Cut, Sorenson Research Co., Salt Lake City, Utah 84115, 3/1979.

Primary Examiner—C. Fred Rosenbaum
Assistant Examiner—J. L. Kruter
Attorney, Agent, or Firm—Martin A. Farber

[57] ABSTRACT

A suction bottle for medical purposes, having an evacuatable inner chamber and a connection nipple for a drainage tube. The connection nipple opens into a disposable bag whose volume can be increased by vacuum and which is arranged within the inner chamber, the collar of said bag being hermetically clamped against the rim of the mouth of the suction bottle.

23 Claims, 7 Drawing Figures

SUCTION BOTTLE FOR MEDICINAL PURPOSES

The present invention relates to a suction bottle for medical purposes, having an evacuatable inner chamber and a connection nipple for a drainage tube.

On the one hand, disposable or single-use suction bottles made of plastic are known. The use of such suction bottles is expensive.

One the other hand, resterilizable suction bottles are known which are intended for repeated use. The sterilization of used suction bottles is, however, also expensive.

The object of the present invention is to provide a suction bottle of the afore-mentioned type which is easy to manufacture and more advantageous in use in that, despite repeated use of the suction bottle, sterilization is not necessary.

This object is achieved by the invention by providing that the connection nipple opens into a disposable bag whose volume can be increased by vacuum and which is arranged within the inner chamber, the collar of said bag being hermetically clamped against the rim of the mouth of the suction bottle.

As a result of this development, a suction bottle of the above-indicated type which is of increased utility is obtained. Despite repeated use of the suction bottle it need not be sterilized. Only the disposable bag contained within the inner chamber comes into contact with the secretions which are to be drawn off. This bag and the collar attached to it are thrown away together with the collar after use, namely after releasing the clamping of the suction bottle against the rim of the mouth. The use of such increasable volume disposable bags provided with a collar is considerably less expensive than the cost of disposable or single-use bottles. The disposable bag whose volume can be increased by vacuum may be made, on the one hand, of stretchable material so that it adapts itself during the suction phase to the shape of the wall of the inner chamber. On the other hand, it is also possible to use disposable bags whose shape is adapted to that of the inner chamber.

The collar of the disposable bag fulfills a twofold function when the collar is further developed as a cover for the suction bottle.

Furthermore, it has been found advantageous if the collar, disposable bag and connection nipple form a single unit. The insertion and the removal of the disposable bag are therefore very easy and can be effected within a short time.

Another advantage resides in the fact that the connection nipple is continued by a tube which extends to the bottom of the bag.

In order to prevent return flow of secretion from the bag into the drainage tube, the lower end of the tube is provided with a valve. This valve may, for instance, be developed in the form of a foil valve.

In order for the cover which closes off the inner chamber to be able to be easily removed even when vacuum is still present in the suction bottle, a valve-actuatable air-inlet opening which opens into the inner chamber is associated with the suction bottle.

The suction bottle is given a robust structural shape by mounting the air-inlet opening, an evacuation connection nipple and a vacuum indicator on the bottom surface of the bottle, with a standing-base collar projecting beyond this bottom surface.

The suction bottle and the standing-base collar preferably are made of transparent material. In this way it is possible both to note the extent to which the disposable bag is full and to read the vacuum indicator.

Undesired equalization of pressure is prevented by making the connection nipple form a sealable section above the collar. This section can also be sealed before the removal of the disposable bag.

For sanitary reasons the connection nipple is provided with a closure cap on the other side of the sealable section. Until the suction bottle is placed in use, it aseptically seals off the connection nipple and the sterile disposable bag.

When the disposable bag is made of certain materials it may be advisable for the inner chamber of the suction bottle to have a groove extending on its inner wall over the length of the inner chamber. Furthermore, if the inner chamber is to be divided into two spaces as a result of a differential expansion of the disposable bag, pressure equalization takes place via the groove.

Another variant of the invention is that the connection nipple bears a pin valve between the closable section and the closure cap. This measure makes it possible to empty the full disposable bag before it is thrown away after the pin valve has been removed.

With the above and other objects and advantages in view, the present invention will become more clearly understood in connection with the detailed description of preferred embodiments, when considered with the accompanying drawings, of which:

Figure 1:
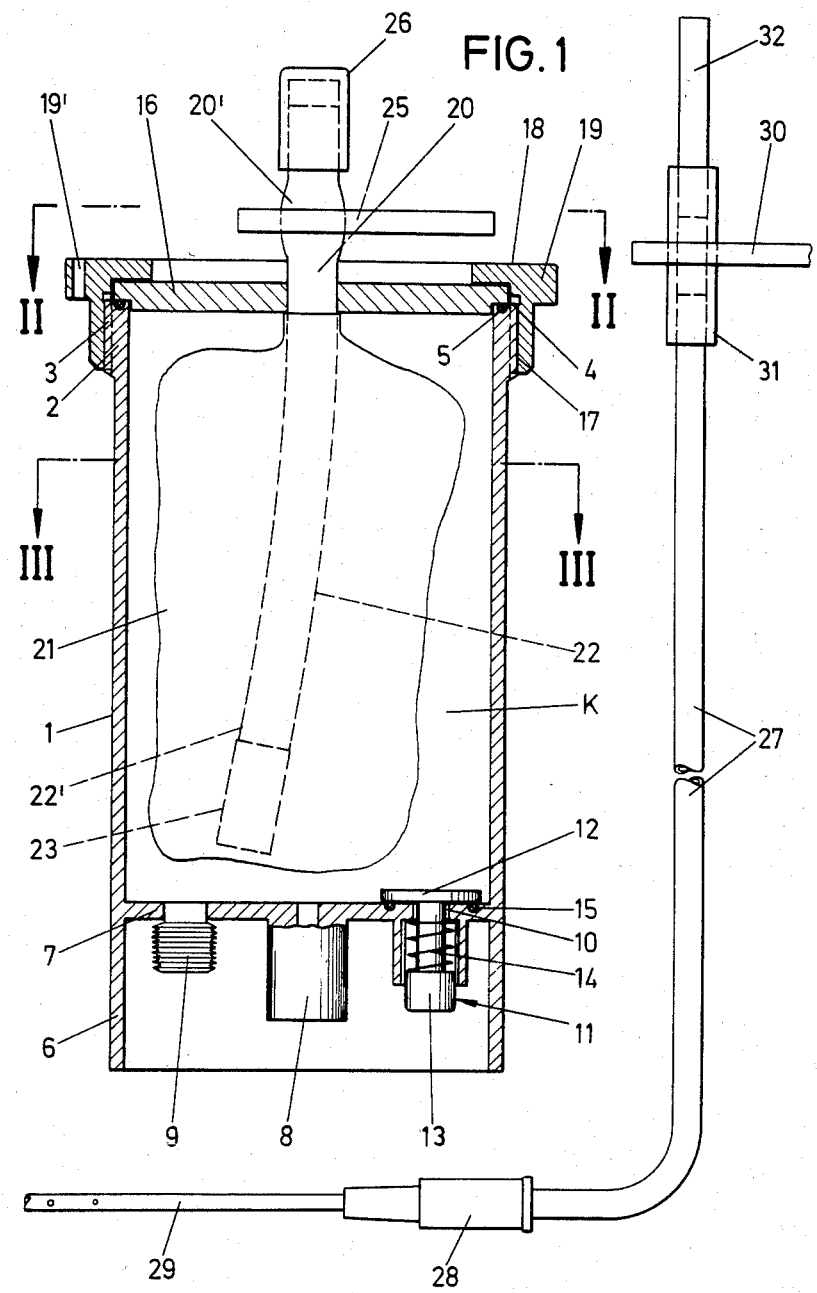
FIG. 1 is a longitudinal section through a suction bottle according to the first embodiment of the invention, containing a disposable bag with its corresponding drainage tube.
Figure 2:
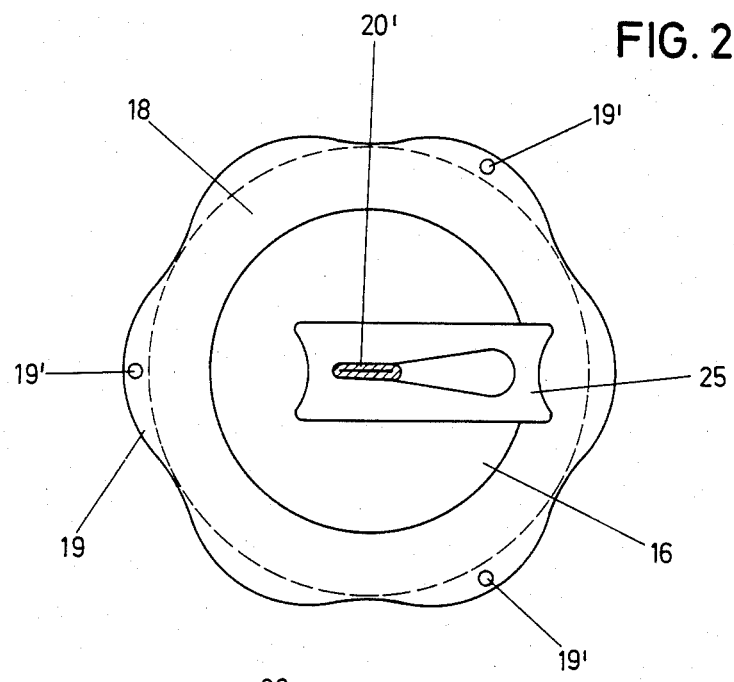
FIG. 2 is a section along the line II—II of FIG. 1.
Figure 3:
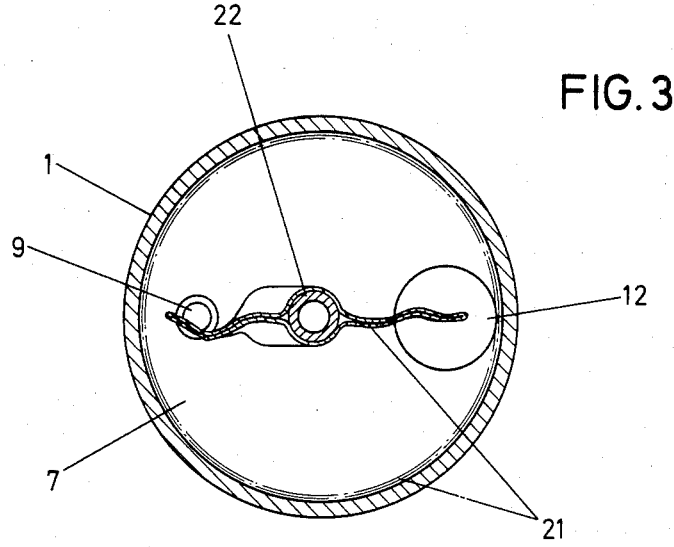
FIG. 3 is a section along the line III—III of FIG. 1.

A cylindrical suction bottle 1 of the first embodiment is provided at its upper end 2 with an external thread 3. The end surface of the rim 4 of the mouth of the suction bottle at the upper end 2 is provided with a flexible sealing ring 5 which protrudes above it.

A standing-base collar 6 extends beyond the bottom surface 7 of the suction bottle. Both the suction bottle 1 and the standing-base collar 6 are made of transparent material. An evacuation connection nipple 8 with valve (not shown) is provided on the bottom surface 7. Adjacent to said nipple and diametrically opposite each other mounted on the bottom surface are a vacuum indicator 9 and an air-inlet opening 10. The latter is closed by a vent valve 11. Components of the vent valve 11 comprise a valve plate 12, an actuating button 13 and a compression spring 14 which biases the valve plate 12 in the closing direction in which it comes against a sealing ring 15 associated with the air inlet opening 10. The evacuation connection nipple 8, vacuum indicator 9 and vent valve 11 are in protected position due to the surrounding standing-base collar 6. A scale can, for instance, be arranged on the standing-base collar 6 for the vacuum indicator 9 so that the vacuum present in the inner chamber K can be read.

The upper closure of the inner chamber K is formed by a cover 16. The edge region of the latter comes against the sealing ring 5 on the rim 4 of the mouth of the suction bottle 1. For clamping the cover 16, a cap nut 18 with an internal thread 17 is provided which is screwed onto the upper end 2. The projecting rim 19 of the cap nut 8 is undulated and serves as a gripping surface. Holes 19' which permit the suction bottle 1 to be hung up are provided on the rim 19.

A connection nipple 20 extends centrally from the cover 16 and opens into a disposable bag 21 which is arranged within an inner chamber K of the suction bottle. The volume of the bag 21 can be increased by producing a vacuum in the chamber K. The cover 16 constitutes the collar of this disposable bag 21. The connection nipple 20 is firmly attached to the cover 16 and continues as a tube 22 which extends down to the bottom of the bag. A valve 23 is provided at the lower end 22' of the tube. The end sealing lips 24 of this valve prevent a return flow of the liquid present in the disposable bag 21.

The collar 16, the connection nipple 20 and the disposable bag 21 form a single unit adapted to be jointly coordinated to the suction bottle 1, the section 20' of the connection nipple 20 which is located above the collar 16 being sealed off by a tube clamp 25. A closure cap 26 is seated on the connecting nipple 20 on the other side of the tube clamp 25.

Figure 4:
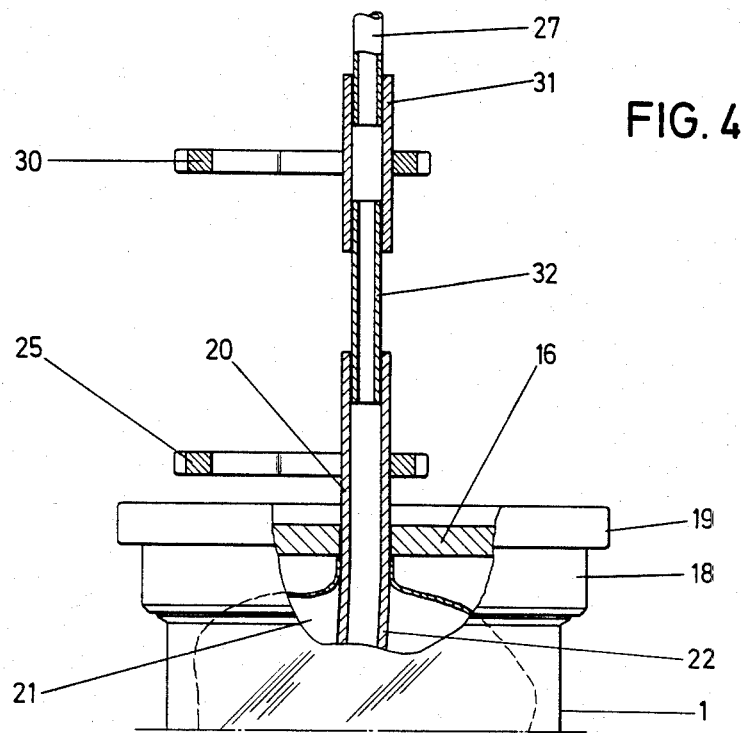
FIG. 4 shows, partly in elevation and partly in section, the upper end of the suction bottle with the drainage tube attached.
Figure 5:
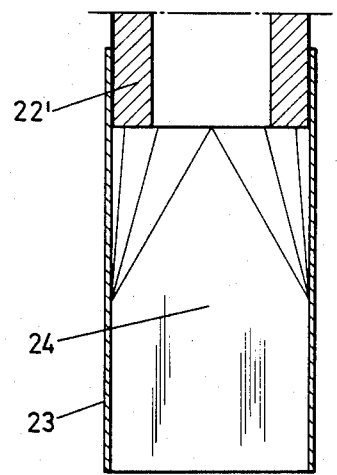
FIG. 5 shows on a much larger scale a longitudinal section through the tube end provided with a valve.
Figure 6:
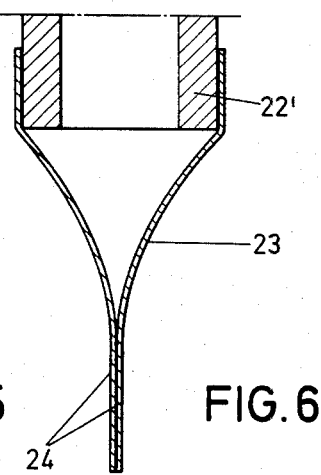
FIG. 6 is a longitudinal section through FIG. 5.

After the insertion of this unit and the removal of the closure cap 26 the drainage tube 27 can be connected. It is connected via a connecting piece 28 to a drainage-tube section 29 adapted to be introduced into a body cavity. The other end of the drainage tube 27 bears a tube section 31 which can be closed by a tube clamp 30 and from which a connecting tube piece 32 extends. The latter is inserted into the connection nipple 20, as shown in FIG. 4. Thereupon the tube clamp 25 is brought into its open position. When the tube clamp 30 has also been brought into the open position, the path from the drainage-tube section 29 to the disposable bag 21 is open. As a result of the vacuum present in the inner chamber K, the volume of the disposable bag 21 can now increase, with the simultaneous production of an aspirating action.

If the disposable bag 21 is to be removed and a certain vacuum is still present in the suction bottle, then the vent valve 11 must be actuated. Furthermore, the tube clamp 25 must be brought into sealing position with respect to the connection nipple 20. Similarly, the tube section 31 must be closed by means of the tube clamp 30. Thereupon, after unscrewing the cap nut 18, the unit comprising the disposable bag 21 with its collar 16 and the joined connection nipple 20 can be removed from the suction bottle and thrown away. The insertion of a new unit of this type, supplied in sterile condition, into the suction bottle is then possible without having to sterilize the suction bottle. After the insertion of the disposable bag, the vacuum can be produced in the inner chamber via the evacuation connection nipple 8. In order to prevent the possibility of confusing the connection nipple 20 with the evacuation connection nipple 8, they are made of different sizes. In order to be able to note the extent to which the disposable bag 21 is full, it may be provided with a scale or graduation. However, it is also possible to provide the suction bottle itself with a graduation.

Figure 7:
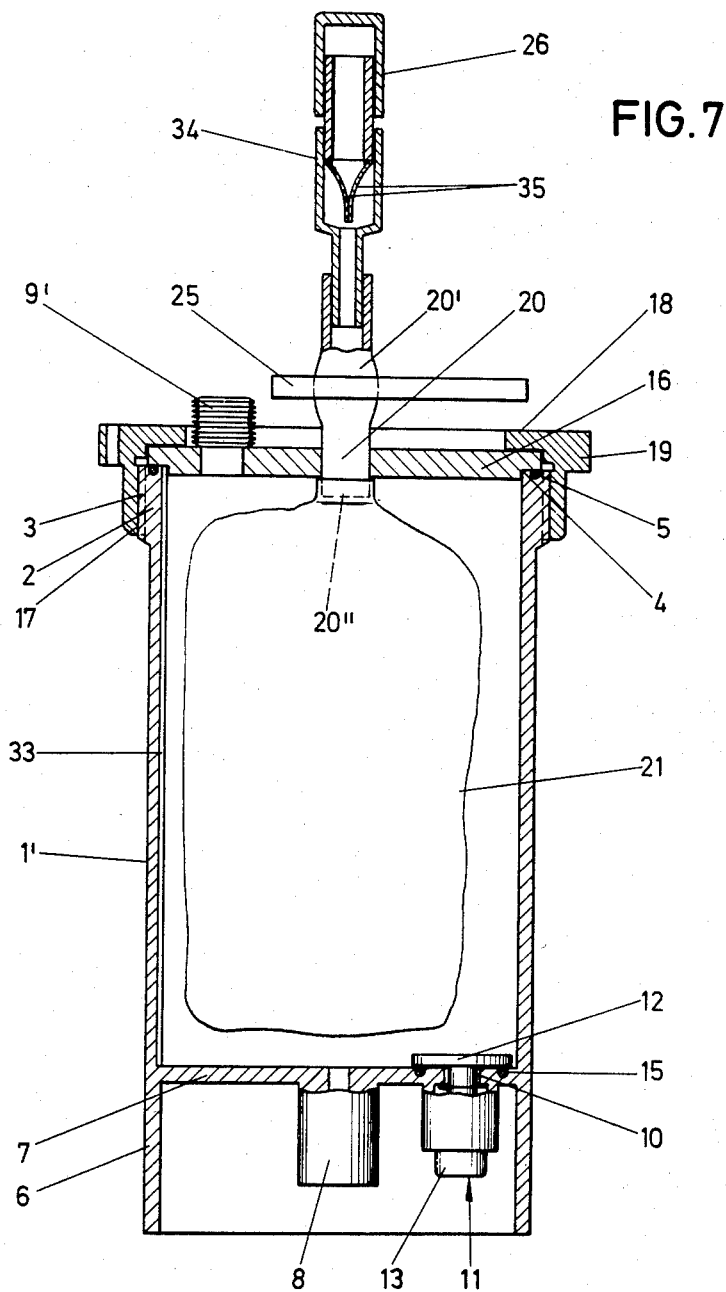
FIG. 7 is a longitudinal section through a suction bottle according to the second embodiment.

Identical parts of the second embodiment shown in FIG. 7 bear the same reference numbers as the previous embodiment. In contradistinction to the first embodiment, the vacuum indicator 9' is now arranged on the cover 16. Furthermore, the inner chamber K of the suction bottle 1' is provided on its inner wall with a groove 33 which extends over the length of the inner chamber.

The connection nipple 20 ccontinues on the inside of the chamber by a short section 20'' thereof for fastening the disposable bag 21. The connection nipple 20 then receives on the other side of its sealable section 20' a pin valve 34 with sealing lips 35 which prevent a return flow of the liquid contained in the disposable bag 21. The closure cap 26 is seated over this pin valve. After removal of this cap, the drainage tube 27 can be connected. When the disposable bag 21 is full, the pin valve 34 can be removed in this embodiment and the disposable bag 21 emptied before it is thrown away.

I claim:

1. In a suction bottle for medical purposes having a cover, with a valve connection nipple for evacuating an inner chamber of the bottle surrounding a disposable bag arranged within the inner chamber, the volume of the bag being increasable by vacuum in the inner chamber outside of the bag adapted to suck material into the bag, a drainage tube connected with the interior of the bag adapted for receiving the sucked material, and an upper edge of the bag suspended at the cover of the suction bottle, the improvement wherein
    said bottle having a bottom wall portion and wall means for supporting the bottle via a part of said wall means such that said bottom wall portion is spaced higher than said part
    the valve connection nipple is arranged at a said bottom wall portion of the bottle,
    means comprising a closure member for air-tight clamping of the drainage tube, and
    a drainage tube connection nipple is provided with said closure member, said drainage tube connection nipple with said drainage tube constitutes sole means of communication into said bag,
    said edge of the bag plus cover plus said drainage tube connection nipple are integrally combined into a disposable unit non-releasably connected air-tightly to each other.
2. The suction bottle according to claim 1, wherein said cover is respectively attachable to and detechable from said bottle and said unit including said cover and said bag is a disposable unit.
3. The suction bottle according to claim 2, wherein said disposable unit includes said drainage tube.
4. The suction bottle according to claim 3, wherein said drainage tube extends from said connection nipple.
5. The suction bottle according to claim 1, wherein said bag is spaced from said evacuation valve in any position of the bottle.
6. The suction bottle according to claim 1, wherein said closure member is a tube clamp on said drainage tube connection nipple for air-tightly clamping the latter and thereby said drainage tube.
7. The suction bottle according to claim 1, wherein said upper edge of the bag is centrally non-linearly attached on said cover circularly arranged around said drainage tube connection nipple.
8. The suction bottle according to claim 1, wherein said suction bottle is formed with an external thread adjacent a rim of a mouth of the suction bottle, said cover is clampable hermetically to said rim of said mouth of said suction bottle, and further comprising a cap nut with internal thread which screws onto said suction bottle at said external thread adapted for clamp the cover.

9. The suction bottle according to claim 8, wherein said cap nut is formed with an undulating projecting rim constituting a gripping surface.

10. The suction bottle according to claim 1, wherein said connection nipple continues as said drainage tube which extends to a bottom of said disposable bag.

11. The suction bottle according to claim 1, further comprising
a valve on a lower end of said tube.

12. The suction bottle according to claim 11, wherein said valve is a foil valve.

13. The suction bottle according to claim 1, wherein a valve-actuatable air-inlet opening opens into said inner chamber of said suction bottle.

14. The suction bottle according to claim 1, wherein said connection nipple forms a sealable section above said cover.

15. The suction bottle according to claim 14, further comprising
a closure cap operatively connected to said connection nipple on a remote side of said sealable section opposite said cover.

16. The suction bottle according to claim 1, wherein said suction bottle has an inner wall which defines said inner chamber, said inner wall is formed with a groove which extends the length of said inner chamber.

17. The suction bottle according to claim 1, wherein said wall means comprises a standing base collar surrounding said valve connection nipple.

18. In a suction bottle for medical purposes having an evacuatable inner chamber and a connection nipple for a drainage tube, the improvement wherein
said suction bottle has a rim of a mouth of the suction bottle,
a disposable bag arranged within said inner chamber,
said connection nipple opens into said disposable bag, the volume of said disposable bag is increasable by vacuum in said inner chamber, and
said disposable bag has a collar which is clamped hermetically to said rim of said mouth of said suction bottle,
a valve-actuatable air-inlet opening opens into said inner chamber of said suction bottle,
said suction bottle has a bottom surface and a standing-base collar extends beyond said bottom surface, said air inlet opening and an evacuation-connection nipple and a vacuum indicator are mounted on said bottom surface of said suction bottle.

19. The suction bottle according to claim 18, wherein said suction bottle and said standing-base collar are made of transparent material.

20. The suction bottle according to claim 18, wherein said connection nipple and said evacuation-connection nipple are of different sizes.

21. In a suction bottle for medical purposes having an evacuatable inner chamber and a connection nipple for a drainage tube, the improvement wherein
said suction bottle has a rim of a mouth of the suction bottle,
a disposable bag arranged within saiid inner chamber,
said connection nipple opens into said disposable bag, the volume of said disposable bag is increasable by vacuum in said inner chamber, and
said disposable bag has a collar which is clamped hermetically to said rim of said mouth of said suction bottle,
said connection nipple forms a sealable section above said collar,
a closure cap operatively connected to said connection nipple on a remote side of said sealable section opposite said collar,
a pin valve between said sealable section and said closure cap operatively communicates with said connection nipple.

22. In a suction bottle for medical purposes having an evacuatable inner chamber and a connection nipple for a drainage tube, the improvement wherein
said suction bottle has a rim of a mouth of the suction bottle,
a disposable bag arranged within said inner chamber,
said connection nipple opens into said disposable bag, the volume of said disposable bag is increasable by vacuum in said inner chamber, and
said disposable bag has a collar which is clamped hermetically to said rim of said mouth of said suction bottle,
a valve-actuatable air-inlet opening opens into said inner chamber of said suction bottle,
a vent valve which closes said valve-actuatable air-inlet opening,
said vent valve comprises a valve plate covering said air-inlet opening, an actuating button connected with said valve plate and a compression spring which moves said valve plate over said air-inlet opening.

23. In a suction bottle for medical purposes having an evacuatable inner chamber and a connection nipple for a drainage tube, the improvement wherein
said suction bottle has a rim of a mouth of the suction bottle,
a disposable bag arranged within said inner chamber,
said connection nipple opens into said disposable bag, the volume of said disposable bag is increasable by vacuum in said inner chamber, and
said disposable bag has a collar which is clamped hermetically to said rim of said mouth of said suction bottle, and
means comprising a valve for stopping air from entering the inner chamber is seated on the suction bottle and provides means for the closure of said disposable bag in order to be able to prepare the suction bottle with vacuum drawn off by a pump and work it without a pump further until the vacuum is exhausted.

* * * * *